United States Patent [19]

Wurster et al.

[11] Patent Number: 4,991,604
[45] Date of Patent: Feb. 12, 1991

[54] ULTRASONIC TREATMENT APPARATUS

[75] Inventors: Helmut Wurster, Oberderdingen; Werner Krauss, Knittlingen; Peter Vallon, Bretten Gölshausen, all of Fed. Rep. of Germany

[73] Assignee: Richard Wolf GmbH, Knittlingen, Fed. Rep. of Germany

[21] Appl. No.: 335,221

[22] Filed: Apr. 7, 1989

[30] Foreign Application Priority Data

Apr. 9, 1988 [DE] Fed. Rep. of Germany ....... 3811872

[51] Int. Cl.$^5$ .............................................. A61B 8/00
[52] U.S. Cl. ............................................... 128/660.03
[58] Field of Search .............................. 606/127, 128; 128/660.03, 24 A

[56] References Cited

U.S. PATENT DOCUMENTS

| | | |
|---|---|---|
| 3,735,755 | 5/1973 | Eggleton et al. |
| 4,526,168 | 7/1985 | Hassler et al. |
| 4,582,065 | 4/1986 | Adams |
| 4,610,249 | 9/1986 | Makofski et al. |
| 4,617,931 | 10/1986 | Dory |
| 4,620,545 | 11/1986 | Shene et al. |
| 4,669,483 | 6/1987 | Hepp et al. |
| 4,705,026 | 11/1987 | Chaussy et al. |
| 4,741,008 | 4/1988 | Franke ........................ 606/128 X |
| 4,763,652 | 8/1988 | Brisson et al. |
| 4,771,787 | 9/1988 | Wurster et al. |
| 4,787,371 | 11/1988 | Grasser et al. ............... 606/128 X |
| 4,787,394 | 11/1988 | Ogura |
| 4,819,621 | 4/1989 | Ueberle et al. .............. 606/127 X |
| 4,821,730 | 4/1989 | Wurster et al. |

FOREIGN PATENT DOCUMENTS

| | | |
|---|---|---|
| 2722252 | 12/1979 | Fed. Rep. of Germany |
| 3119295 | 12/1982 | Fed. Rep. of Germany |
| 3122056 | 12/1982 | Fed. Rep. of Germany |
| 3220751 | 12/1983 | Fed. Rep. of Germany |
| 3319871 | 12/1984 | Fed. Rep. of Germany |
| 3544344 | 6/1987 | Fed. Rep. of Germany |
| 3621935 | 1/1988 | Fed. Rep. of Germany |
| 2140693 | 12/1984 | United Kingdom |

OTHER PUBLICATIONS

D. J. Coleman, F. L. Lizzi, and F. A. Jakobiec, "Therapeutic Ultrasound in the Production of Ocular Lesions," Am. J. Ophth., 86:185, 1978.

D. J. Coleman, F. L. Lizzi, A. A. M. El-Mofty, J. Driller, and L. A. Franzen, "Ultrasonically Accelerated Resorption of Vitreous Membranes," Am. J. Ophth., 89:490, 1980.

D. J. Coleman, F. L. Lizzi, S. Chang, and J. Driller, "Applications of Therapeutic Ultrasound in Ophthalmology," Prog. in Med. Ultrasound, vol. 2, 1981, p. 263.

"Chapter IV, The L.T.01. Lithotripter: EDAP," Lithotripsy II, Coptcoat, Miller and Wickham, eds., pp. 57–62 (Sep. 1987).

Wurster, Ziegler and Marberger, "Chapter VI, Piezolith 2200 (Richard Wolf Gmbh)," Lithotripsy II, Coptcoat, Miller and Wickham, eds., pp. 91–107 (Sep. 1987).

Primary Examiner—Francis Jaworski
Attorney, Agent, or Firm—Panitch Schwarze, Jacobs & Nadel

[57] ABSTRACT

Apparatus for the detection and destruction by means of ultrasonic shock waves of an object within the body, comprises a transducer operated by a pulse generator for emitting shock waves which are focussed on the body of the patient by way of a fluid coupling medium. A location system connected to the transducer comprises at least one monitor as a display device. The monitor has a screen for depicting an image of the object and an aiming or sighting mark which can be placed in coincidence with the object by relative displacement between the patient and the transducer to position the focus of the transducer on the object and to authorize the operation of the pulse generator. A signal level corresponding to the brightness value of the object depicted on the screen, and obtained from a video signal of the location system, is established as a reference value. A selected target area including the object, can be scanned automatically by displacement of the transducer. The video signals produced concomitantly in the imaging system are compared as actual values with the reference value and the pulse generator is operated when the level of the actual values is at least equal to the level of the reference value.

16 Claims, 4 Drawing Sheets

ULTRASONIC TREATMENT APPARATUS

FIELD OF THE INVENTION

This invention relates to apparatus for the detection and destruction of an object in a body of a patient to be treated, by means of ultrasonic shock waves, the apparatus comprising; an ultrasonic pulse generator actuable to initiate said shock waves, an ultrasonic transducer associated with said pulse generator for focussing said shock waves onto said object by way of a fluid coupling medium; an object location system connected to said transducer and having at least one monitor in the form of a display device provided with an image screen, for depicting on said screen, an image of said object and an aiming mark capable of being brought into coincidence by relative movement of said patient and said transducer to position the focus thereof on said object; and means for authorising the actuation of said pulse generator when said image and said aiming mark have been brought into coincidence.

BACKGROUND OF THE INVENTION

Apparatus as described above are in clinical use, and typical examples thereof are disclosed for example, in DE-A-33 19 871, DE-A-27 22 252 and DE-B-31 19 295.

In such apparatus, focussed ultrasonic shock waves are aimed at a concretion, that is to say a solid mass of foreign material, present within an organ of the body, to destroy the concretion, thereby removing it by a non-surgical method. After such treatment only a fine grit remains in said organ, which is for example a kidney, and such grit is flushed from the body naturally.

Before triggering a firing sequence of comparatively powerful ultrasonic waves, the precise location of the concretion which is to be destroyed must be established. An A scanner and/or a B scanner are commonly used for this purpose.

A problem that occurs during the use of such apparatus is that healthy tissue adjacent to the concretion may be damaged by the action of the ultrasonic shock waves, if the focus of the ultrasonic transmission system does not coincide with the concretion or tissue (where said object is tissue) to be destroyed.

The accuracy required in positioning the focus with respect to the object to be destroyed, for example a kidney stone, depends among other things upon the principle according to which the ultrasonic waves are generated. If, for example, the shock waves are generated according to the known submerged arc discharge principle and are focussed by means of ellipsoidal reflectors, the focal point diameters typically so obtained are of the order of magnitude of approximately 10 mms. Since such a focal point diameter is large in relation to a stone of the usual size, no great precision in positioning the focus is then needed.

If, however, the ultrasonic shock waves are generated by means of better focussed sources of shock waves, for example by means of piezoelectric transducers according to DE-A-33 19 871, focal point diameters are obtained which only have an order of magnitude of approximately 2 mms. The ratio between the size of the stone and the focal point diameter is, therefore, smaller than where the shock waves are generated according to said arc discharge principle as discussed above. Precise positioning of the focus is, therefore, needed in order to prevent injury to the tissue surrounding the stone where a sequence of shock wave pulses is triggered at an instant when the focus does not coincide with the stone.

Even where such a small diameter focus has been positioned so as to coincide with a stone to be destroyed, it cannot be assumed that the stone will remain in its initial position throughout the ultrasonic treatment.

The concretion, in this case the stone, which is to be destroyed can alter its position under the influence of cyclically recurrent bodily functions and in particular as a result of the patient's respiration, and the position of the stone may also be altered by the initial ultrasonic bombardment of the stone.

Thus, the triggering of sonic pulse sequences should be avoided in such a case, where the concretion to be destroyed leaves the originally correctly positioned focus of the ultrasonic transmitter as a result of a bodily function. DE-A-36 21 935, for example, discloses a triggering system which controls the firing sequence as a function of a bodily activity, that is to say as a function of a comparison between a threshold value and an actual value.

Shock waves may be applied not only for the destruction of concretions, but also for sealing off blood vessels for example by a clotting action, or for the direct destruction of unhealthy tissue such as tumours, according to DE-A-35 44 344. Substantially the same problem that occurs in the destruction of concretions also arises in these other cases, namely that care should be taken to ensure that adjacent healthy tissue is not impaired by the ultrasonic shock waves. Triggering systems which are controlled by a bodily function, are, however, applicable only where said function is recurrent, and are, therefore, for controlling the release of shock waves as a function of an isolated event, for example the shifting of an object to be destroyed in the body after an initial ultrasonic bombardment, or the movement of the patient on the operating table.

SUMMARY OF THE INVENTION

It is, therefore, an object of the present invention to provide apparatus for the detection and destruction by ultrasonic means, of objects within the body, that is arranged to authorise the triggering of ultrasonic shock waves only when said object is positioned at the focus of the ultrasonic transmitter system, the handling of the apparatus that is to say, the location of the object to be destroyed being reliable and compatible with the user.

According to the invention, a signal level corresponding to the brightness value of the object depicted on the screen of the display device, and obtained from a video signal of the location system is established as a reference value, a selected target area including the object to be destroyed is arranged to be scanned automatically by displacement of the transducer, video signals produced by the location system are compared as actual values with said reference value and the pulse generator operating the transducer is actuated when the level of the actual values are at least equal to the level of the reference value.

The apparatus is, therefore, so constructed that a signal level corresponding to the brightness value of the object depicted, and obtained from a video signal generated by an imaging system (for example a B scanner) can be established as a nominal or reference value, that a selected target area including the object to be destroyed can be scanned automatically by shifting the transducer, that the video signals concomitantly occuring in the imaging system can be compared as actual values to the reference value, and that the pulse generator for energising the ultrasonic transducer is actuated when the level of the actual values is at least equal to the level of the reference value.

The location system need not be an imaging system based on ultrasonic technology but said imaging system may be an X-ray location system.

The coordination of the automatic scanning of the target area by displacement of the transducer, with the authorization of the actuation of the pulse generator, when the measured brightness level exceeds the present reference value, facilitates the operation of the apparatus by the personnel concerned and ensures safe operation of the apparatus, since the pulse generator cannot be actuated in the event of doubtful coincidence between the position of the object to be destroyed and the focus of the ultrasonic transducer, so that healthy tissue is protected form damage by shock waves near said object.

The reference value should be less than the value corresponding to the actual brightness of the object depicted since the actual brightness value may be specifically reduced by the formation of particles and/or stone dust, to the extent that, if the reference value is too high, the pulse generator is prematurely deactivated so that a stone to be destroyed cannot be completely disintegrated.

According to an embodiment of the invention, the video signals are transmitted graphically and the coordinates of the aiming mark position which vary with the displacement of the transducer are transmitted by means of a memory, the image signals associated with the position of the aiming mark being read out of the memory. These image signals are supplied as actual values to one input terminal of a comparator circuit, the other input terminal of which receives a signal corresponding to the reference value. A control system for blocking or authorizing the operation of the pulse generator is connected to the output terminal of the comparator circuit which serves to compare the actual values and reference value.

The displacement and the positioning of the transducer are advantageously detected by means of position sensors cooperating with motorized drive means for the transducer, said sensors being connected to the inputs of said control system.

The displacement of the transducer may be preset and programmed. To this end, the transducer may be movable within an X,Y plane defined by a preset target area, for the purpose of automatic scanning, or an authomatically scannable target area may be preset, the transucer then being displaceable along X,Y and Z co-ordinates.

The imaging system may have at least one B scanner forming a structural unit with the transducer and may be rotatable and axially displaceable with respect to the transducer.

Alternatively, the imaging system may comprise at least one B scanner, the transducer being displaceable with respect to the B scanner, the B scanner remaining stationary. To this end, the transducer is preferably pivotally mounted about two axes, for automatic scanning operation, so that circular or elliptical trajectories of the transducer can be induced by matching or adjusting the angular speeds of the pivotal displacements of the transducer.

The focus of the transducer may be pivotally displaceable on discretionary trajectories extending in the direction of a common centre about the axis of symmetry of the transducer, to locate the object to be destroyed in the target area.

Since displacement of the transducer may be effected not only by means of one or more pivot spindles but also by means of telescopically displaceable bearings, at least three bearings receiving the transducer may be axially displaceable to effect a controlled pivotal and/or wobbling movement of the transducer.

Preferably, the aiming mark continuously represents the focus of the transducer on the monitor, irrespective of the displacement of the transducer.

DETAILED DESCRIPTION OF THE INVENTION

Figure 1:
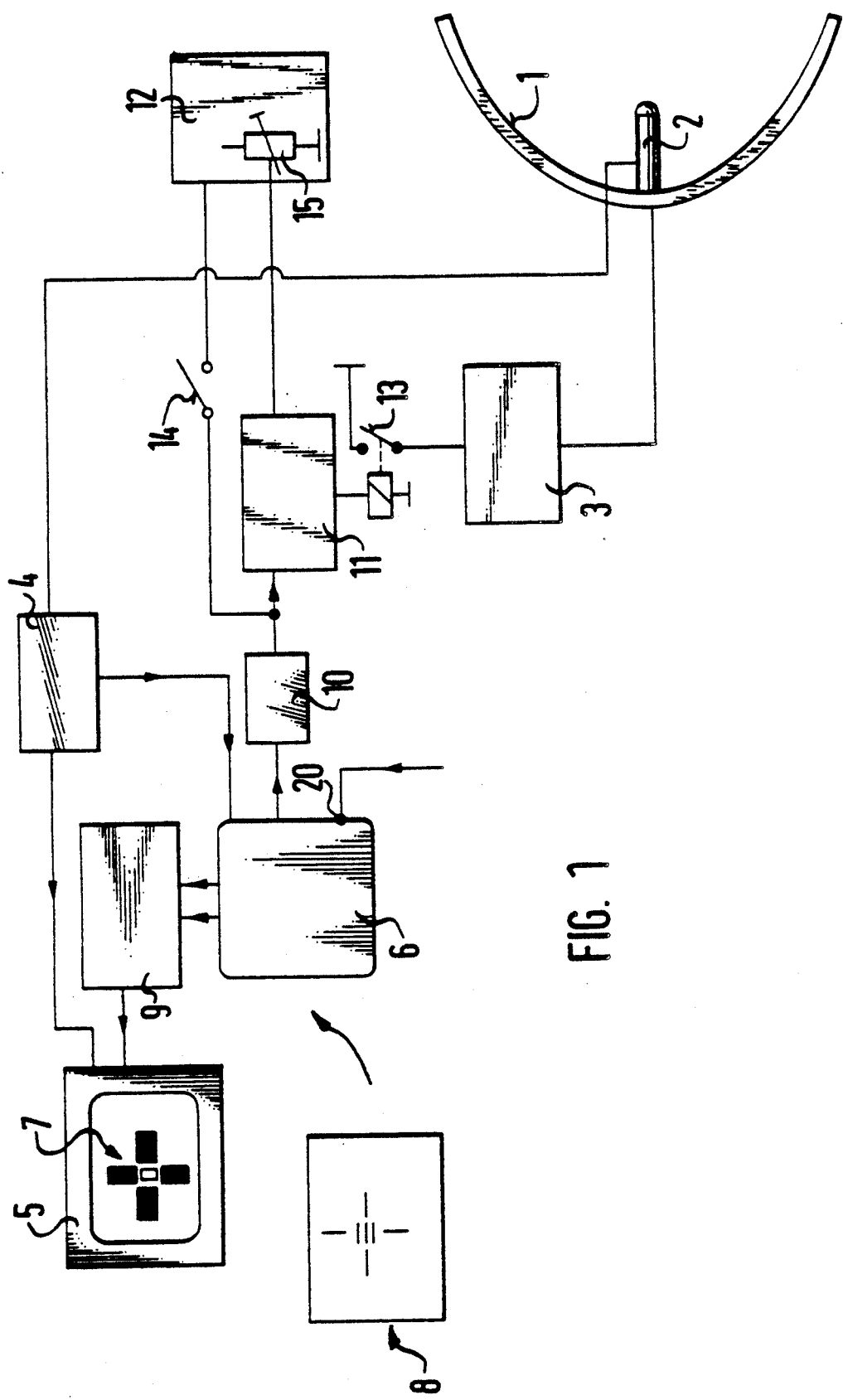
FIG. 1 is a block schematic circuit diagram of apparatus according to a first embodiment of the invention for the detection and destruction of objects within the body of a patient to be treated.

As shown in FIG. 1 an ultrasonic transducer 1 is fixed to an ultrasonic scanner 2. The transducer 1 is activated by a pulse generator in the presence of an authorization signal, as described below.

An ultrasonic signal received by the scanner 2 has its brightness detected by means of a brightness detecting meter 4 and is displayed on a monitor 5 connected to the meter 4. The brightness values of the ultrasonic signal measured by the meter 4, and fed to a matrix memory 6 for storage therein.

The position of an aiming or sighting mark 7 on a two-dimensional image depicted on an image screen of the monitor corresponds to the position of a virtual sighting mark 8 in the matrix memory 6. The mark 8 in the matrix memory 6 serves the purpose of addressing a two-dimensional field of ultrasonic scanner signal brightness values stored in the matrix memory 6.

A sighting mark control system 9 between the matrix memory 6 and the monitor 5, ensures that the sighting mark 7 delimits precisely the same area on the image screen as that addressed by the virtual sighting mark 8 in the matrix memory 6.

The position of the sighting mark 8 in the matrix memory 6 and thereby indirectly that of the sighting mark 7 of the monitor 5, is adjustable by means of an appropriate signal which is fed to the matrix memory 6 via an input 20 as described below.

The contents of the matrix memory 6 within the field delimited by the virtual sighting mark 8 are fed to a mean value generator 10 which determines a mean value for the brightness readings of all matrix dots lying within the field of said sighting mark. The value so established is fed to a comparator 11 which also receives a predetermined reference value from a reference value memory 12.

The reference value is so determined that after energising a reset switch 14, the actual value of the averaged brightness values of the image dots encompassed by the sighting mark 8 in the matrix memory 6 in respect of a sighting mark position at which the object to be destroyed lies within the target area and thereby yields the maximum brightness values, is stored in the memory 12. When the actual value of the brightness level applied to the comparator 11 is at least equal to the level of the reference value derived from the memory 12, a release or authorising switch 13 connected to a pulse generator 3 is activated, thereby enabling shock waves to be delivered to the object to be destroyed and which is present at the focus.

By virtue of the circuit just described, authorisation to trigger an ultrasonic shock wave by way of transducer 1 is issued only when the object to be destroyed lies within the target area, that is to say within the focal area of the transducer 1.

The reference value stored in the memory 12 is adjustable by means of a setting device 15, in such a way that the reference value lies below the value corresponding to the actual brightness value of the object depicted, when it is in the target area. The reference value is preferably selected so as to be 0.8 times the actual brightness value. This is relevant if the actual value of the brightness is reduced to a specific extent after the initial application of the shock waves, by the formation of particles and stone dust. If the reference value applied were too high in such a case, being, for example 100% of the maximum brightness value prior to the application of shock waves, the transducer 1 could be turned off prematurely by the system if the reference value were reached too rapidly, thereby preventing the further application of shock waves to the concretion, so that it cannot be completely destroyed.

Means for automatic scanning of the target area by displacement of the transducer 1 will now be described with reference to FIG. 2.

The displacement of the transducer 1 by means of the ultrasonic scanner 2 fixed thereto is performed by means of electric motors $M_xM_yM_z$ controlled by a logic system motor amplifier 16. The amplifier 16 receives signals from a calculator 17 which in turn receives input signals from an input signal unit 18.

The co-ordinates $X_1$, $X_2$, $Y_1$, $Y_2$, $Z_1$ as well as $\Delta X$, $\Delta Y$ and $\Delta Z$ are fed into the input unit 18, the suffixed co-ordinates representing the coordinates of a volumetric element encompassing the object to be destroyed, and the $\Delta$ values the corresponding intervals during the scanning action.

The values fed to the unit 18 are supplied to a program stored in the calculator 17, which thereupon determines the course of the displacement of the transducer 1. The logic system motor amplifier 16 is controlled accordingly by the calculator 17.

Figure 2:
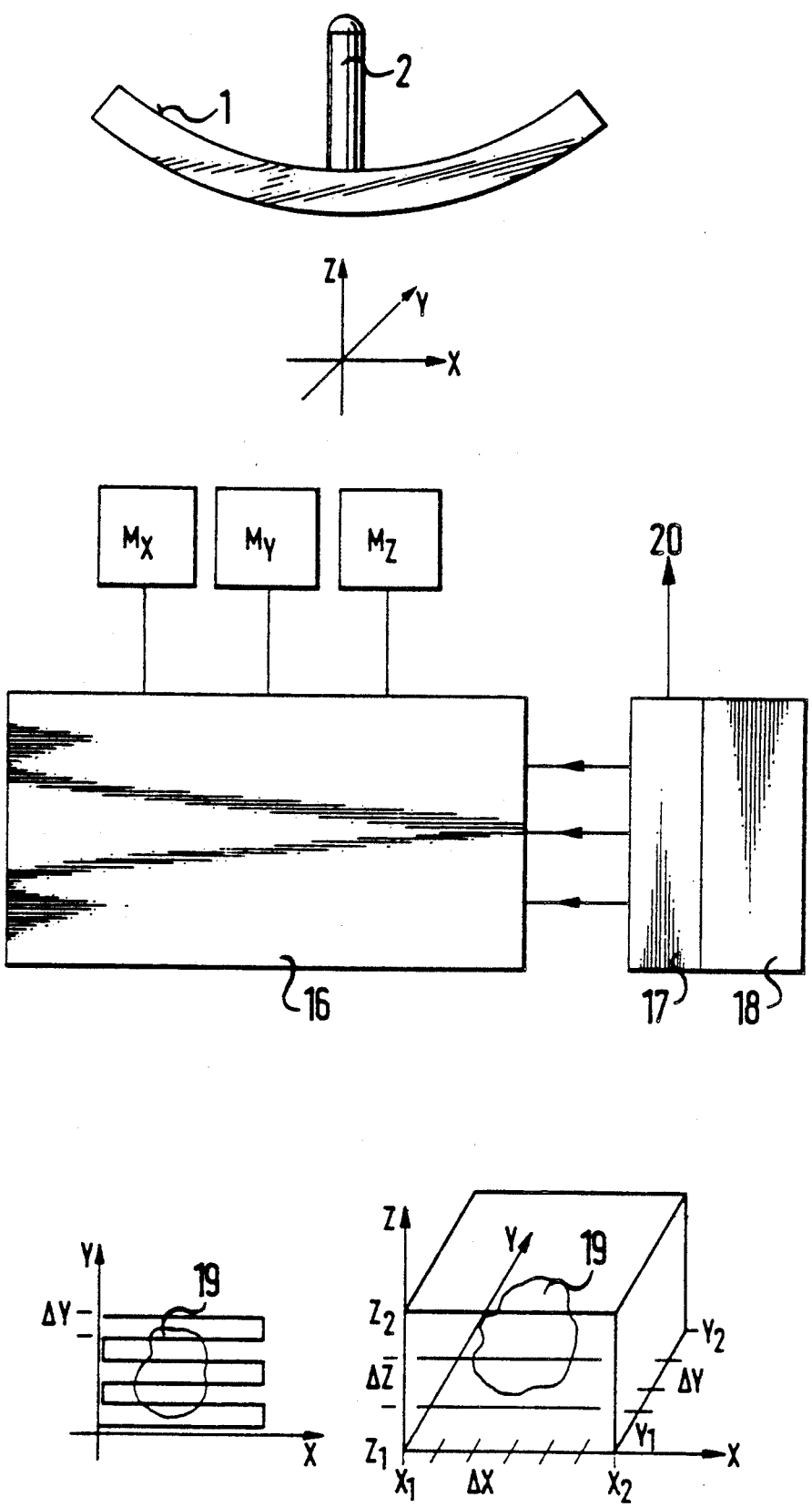
FIG. 2 is a block schematic diagram of a control system for a motor of the apparatus, by means of which a transducer thereof scans a target area, and shows said target area diagrammatically both in two-dimensional and three-dimensional form.

Examples of the automatic movements of the transducer 1 in scanning an object 19 to be destroyed are illustrated diagrammatically at the bottom of FIG. 2, the illustration at the bottom of the left hand side of FIG. 2 merely indicating a two dimensional scanning action of the transducer 1 in the X,Y, direction, whereas the bottom right hand illustration in FIG. 2 also indicates a scanning action of the transducer in the Z direction.

Since the focal length of the transducer 1 commonly has an approximate order of magnitude of 10 mms and since this corresponds to the order of magnitude of most objects which are to be destroyed, two-dimensional scanning action of the transducer 1 is usually adequate.

The co-ordinates fed into the input signal unit 18 are supplied by way of the calculator 17 to the matrix memory 6 (FIG. 1) by way of its input terminal 20. It is thereby assured that the position of the sighting mark 7 of the monitor 5 as well as that of the virtual mark 8 of the matrix memory 6 vary according to the displacement of the transducer 1 and that the marks 7 and 8 always represent the focal area of the transducer 1.

If the object to be destroyed moved out of the target area during the application of the apparatus as described above, the authorisation for the application of the shock waves is stopped automatically until the position of the object to be destroyed has been determined by the automatic scanning of the target area, so that a further authorisation can then be established for the application of the shock waves on the basis of the brightness level detection operation performed on the target area.

The second embodiment of the invention, enabling the automatic scanning of the target area of the object to be destroyed, will now be described with reference to FIGS. 3 and 4, in which parts described above with reference to FIGS. 1 and 2 bear the same reference numerals.

Figure 3:
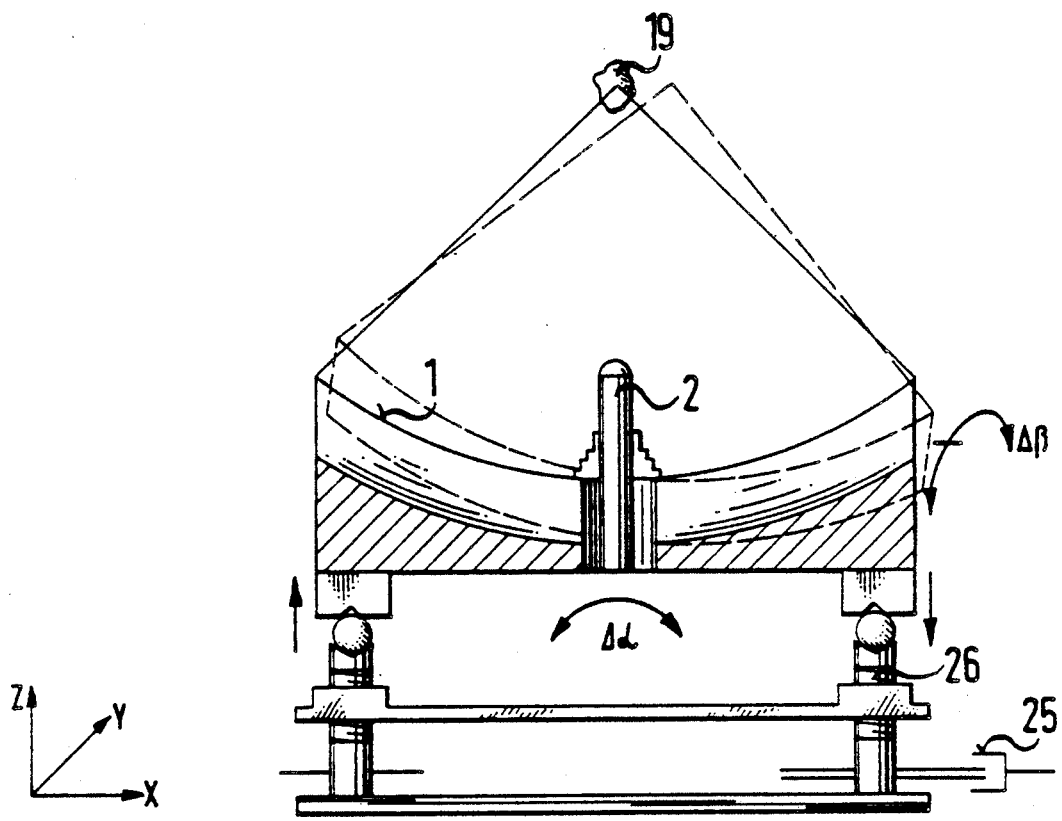
FIG. 3 is a diagram of a structure according to a second embodiment of the invention for tilting the transducer whilst an ultrasonic scanner of the apparatus remains stationary.
Figure 4:
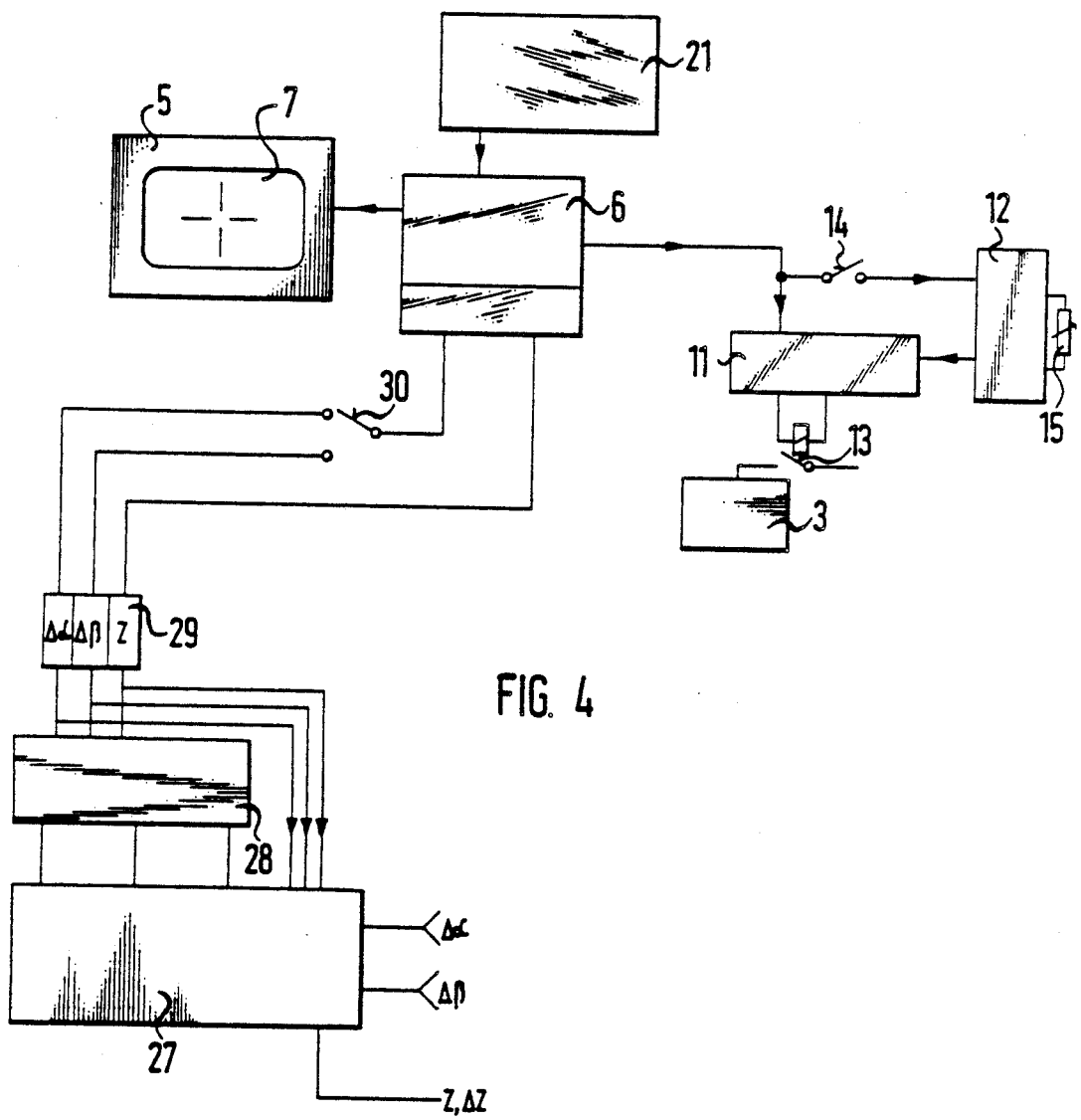
FIG. 4 is a block schematic circuit diagram of a control system for the embodiment of FIG. 3.

As shown in FIG. 3 an ultrasonic transducer 1 has an ultrasonic scanner 2 which remains stationary during displacement of the transducer 1. The transducer cup is mounted for pivotal movement about a center through a small angle $\Delta\alpha$ and $\Delta\beta$ in relation to the axes X and Y, respectively. To this end, the transducer cup can be moved up and down by means of at least three, preferably four screw-threaded rods 26 for example, these being driven for example by an electric motor (not shown) for this purpose.

The cup is similarly mounted with respect to the other axis, so that a circular or an eliptical movement results from the superimposition of the cup movements. The displacement in the Z direction described by the transducer 1 is modulated in respect of time so that an ellipse is always traversed from zero to maximum value of Z in a spiral manner, said maximum value being adjustable.

The circuit shown in FIG. 1 is used to authorise a shock wave pulse. To this end, the marks 7 and 8 of the oscillating mvoement described by the transducer 1 must be guided accordingly.

The input of the displacement angles $\Delta\alpha$, $\Delta\beta$ and the co-ordinate Z of $\Delta Z$, is performed by means of a control system 27 (FIG. 4) which energises electric motors 28. The co-ordinate position momentarily occupied by the transducer 1 is detected by position sensors 25 (FIG. 3) and conveyed to the matrix memory 6 by way of transmitters 29. A switch 30 serves for switching over the ultrasonic plane as a function of the image setting of the ultrasonic scanner 2. To this end, pivotal movement through the angle $\Delta\alpha$ is correlated with an illustration in the X-Y plane and one through the angle $\Delta\beta$ is correspondingly correlated with an illustration in Y-Z plane.

The electronic circuit for controlling the triggering of the shock wave pulses corresponds to the circuit of FIG. 1. An ultrasonic image generation device 21 (FIG. 4) for example a B scanner, is shown only diagrammatically.

The transducer cup according to the second embodiment need not be mounted on screw-threaded rods (such as the rods 26 in FIG. 3) but the cup may be installed on at least three mountings which are axially displaceable to effect a controlled pivotal and/or wobbling displacement of said cup.

What is claimed is:

1. Apparatus for the detection and destruction of an object in a body of a patient to be treated, by means of ultrasonic shock waves, the apparatus comprising; an ultrasonic pulse generator actuable to initiate said shock waves, an ultrasonic transducer associated with said pulse generator for focussing said shock waves onto said object by way of a fluid coupling medium; an object location system connected to said transducer and having at least one monitor in the form of a display device provided with an image screen, for depicting on said screen, an image of said object and an aiming mark capable of being brought into coincidence by relative movement of said patient and said transducer to position the focus thereof on said object; and means for authorising the actuation of said pulse generator when said image and said aiming mark have been brought into coincidence; the apparatus further comprising; means for obtaining from a video signal of said location system, a signal having a level corresponding to the brightness of said object depicted on said screen to establish a reference value, means for automatically displacing said transducer to scan said object; a comparator for comparing as actual values, video signals produced in said location system, with said reference value; and means for actuating said pulse generator when said actual values are at least equal to said reference value.

2. Apparatus as claimed in claim 1, comprising means for adjusting said reference value so that said reference value lies below the actual brightness value of said object depicted on said screen.

3. Apparatus as claimed in claim 1, comprising means for transmitting said video signals in graphic form; a control circuit comprising a memory; means for transmitting to said control circuit co-ordinates of the position of said aiming mark, means for supplying to a first input of said comparator, as actual values, signals from said memory indicative of the position of said aiming mark; means for supplying to a second input of said comparator a signal corresponding to said reference value, and a control system for blocking, and for authorising, the actuation of said pulse generator in dependance upon the comparison between said actual values and said reference value.

4. Apparatus as claimed in claim 1, comprising drive motor means for displacing said transducer; and sensors for cooperation with said drive motor means to detect displacements and positions of said transducer and being connected to inputs of said control system.

5. Apparatus as claimed in claim 1, comprising means for programming predetermined movements of said transducer.

6. Apparatus as claimed in claim 1, comprising means for automatically displacing said transducer in an Y-X plane defined by a predetermined ultrasonic shock wave aiming area to cause said transducer to scan said area.

7. Apparatus as claimed in claim 1, comprising means for automatically displacing said transducer with respect to X, Y and Z coordinates for scanning an ultrasonic shock wave target area.

8. Apparatus as claimed in 1, wherein said location system comprises at least one B scanner forming a structural unit with said transducer, said transducer being rotatable and axially displaceable with respect to said B scanner.

9. Apparatus as claimed in claim 1, wherein said location system comprises at least one B scanner and means for displacing said transducer with respect to said B scanner.

10. Apparatus as claimed in 9, wherein said transducer is mounted for movement about two axes, for automatically scanning an ultrasonic shock wave aiming area, the angular velocities of the pivotal movements of said transducer being adjustable to move the focus of said transducer through arcuate trajectories.

11. Apparatus as claimed in claim 10, wherein said angular velocity is adjustable to move said focus through an elliptical trajectory.

12. Apparatus as claimed in claim 10, wherein said angular velocity is adjustable to move said focus through a circular trajectory.

13. Apparatus as claimed in claim 1 comprising means for pivotally displacing the focus of said transducer along paths extending in the direction of a common center, about the axis of symmetry of the transducer for locating said object in an ultrasonic shock wave target area.

14. Apparatus as claimed in claim 1, wherein the transducer is mounted to at least three bearings which are axially displaceable to bring about a pivotal movement of the transducer.

15. Apparatus as claimed in claim 1, wherein the transducer is mounted to at least three bearings which are axially displaceable to bring about a wobbling movement of the transducer.

16. Apparatus as claimed in claim 1, comprising means for displacing said transducer and wherein said aiming mark depicted on said screen depicts the focus of said transducer in any position thereof.

* * * * *